(12) United States Patent
Van Asseldonk et al.

(10) Patent No.: US 11,235,092 B2
(45) Date of Patent: Feb. 1, 2022

(54) EXPRESSION KIT

(71) Applicant: KONINKLIJKE PHILIPS N.V., Eindhoven (NL)

(72) Inventors: Johannes Petrus Antonius Maria Van Asseldonk, Eindhoven (NL); Alexander Van Rooijen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 555 days.

(21) Appl. No.: 16/084,029

(22) PCT Filed: Mar. 6, 2017

(86) PCT No.: PCT/EP2017/055115
§ 371 (c)(1),
(2) Date: Sep. 11, 2018

(87) PCT Pub. No.: WO2017/157701
PCT Pub. Date: Sep. 21, 2017

(65) Prior Publication Data
US 2020/0289729 A1 Sep. 17, 2020

(30) Foreign Application Priority Data
Mar. 15, 2016 (EP) .................................... 16160500

(51) Int. Cl.
*A61M 1/06* (2006.01)
*A61M 39/24* (2006.01)

(52) U.S. Cl.
CPC ............ *A61M 1/064* (2014.02); *A61M 1/062* (2014.02); *A61M 39/24* (2013.01); *A61M 2039/2426* (2013.01)

(58) Field of Classification Search
CPC ......... A61M 1/064; A61M 1/06; A61M 1/066
See application file for complete search history.

(56) References Cited

U.S. PATENT DOCUMENTS

| | | |
|---|---|---|
| 3,756,198 A | 9/1973 | Rudle |
| 8,827,947 B2 | 9/2014 | Bosman |
| 2013/0046234 A1* | 2/2013 | Van Eijkelenborg ........................ A61M 1/0031 604/74 |
| 2014/0121593 A1 | 5/2014 | Felber |
| 2014/0288466 A1 | 9/2014 | Alvarez |
| 2016/0256617 A1* | 9/2016 | Hansen ................... A61M 1/06 |

FOREIGN PATENT DOCUMENTS

| | | |
|---|---|---|
| WO | 2012049606 A1 | 4/2012 |
| WO | 2014045169 A1 | 3/2014 |
| WO | 2014063261 A1 | 5/2014 |

* cited by examiner

Primary Examiner — Emily L Schmidt

(57) ABSTRACT

The present invention relates to an expression kit (1) for extraction of breast milk from a female breast, comprising a funnel (2) for receiving the breast therein, a housing (4), a container (5) for receiving the breast milk, a connection port (7) for connection to a vacuum source, and a membrane element (6) arranged in the housing (4) between the funnel (2) and the container (5) for sealing the funnel (2) with respect to the connection port (7), the funnel (2) with respect to the housing (4) and the housing (4) with respect to the container (5).

19 Claims, 4 Drawing Sheets

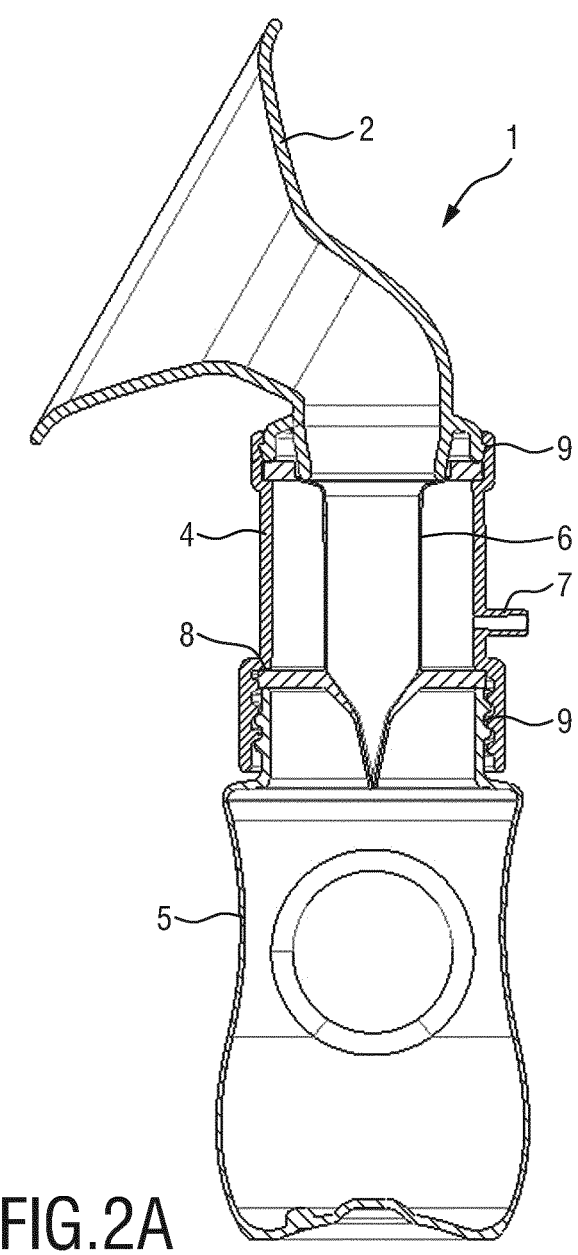
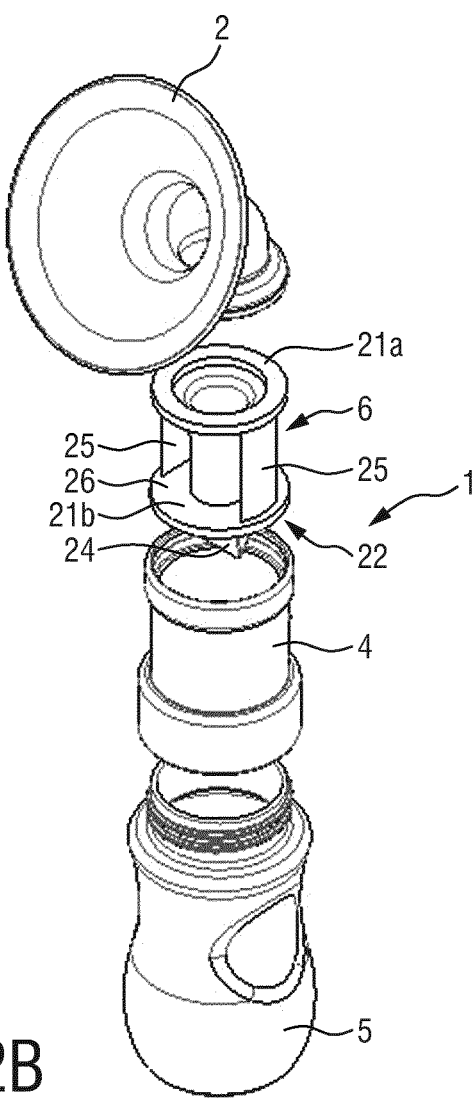
FIG.2A
FIG.2B

EXPRESSION KIT

This application is the U.S. National Phase application under 35 U.S.C. § 371 of International Application No. PCT/EP2017/055115, filed on Mar. 6, 2017, which claims the benefit of International Application No. 16160500.1 filed on Mar. 15, 2016. These applications are hereby incorporated by reference herein.

FIELD OF THE INVENTION

The present invention relates to an expression kit for a breast pump for extracting milk from a female breast.

BACKGROUND OF THE INVENTION

Expression kits for breast pumps normally comprise a body with an integrated funnel to receive the breast therein. Since breasts are different depending on the state of lactation, different funnels will be necessary, leading to large parts which are difficult to produce and to clean. This problem might be solved by funnels which are detachable from the body. This, however, leads to the problem of an airtight sealing between the funnel and the body.

Likewise, modern breast pumps contain a membrane to seal the vacuum source with respect to the milk flow path in the expression kit. The membrane is typically located on the top of the expression kit, making it bulky and less attractive in design. In addition, when the funnel is made of transparent plastics to allow the user to control the position of the nipple, the membrane covers clear view.

The membrane is in contact with the expressed milk and thus needs to be sterilized. In known expression kits, the membrane is of complicated shape which makes cleaning difficult. The additional part which houses the membrane is difficult in shape and thus costly to produce.

US 2014/0288466 A1 discloses a device for expression and collection of breast milk includes an actuatable assembly, a breast interface, and a tube. The breast interface is sized to receive a breast and form a fluid tight seal against the breast. The breast interface includes a deformable member disposed within at least a portion of the breast interface. The deformable member deforms in response to actuation of the actuatable assembly and applies vacuum pressure against the breast to express milk. The tube operatively couples the actuatable assembly to the breast interface.

SUMMARY OF THE INVENTION

It is an object of the present invention to provide a expression kit which is easy to assemble, to use and to clean and cost effective in production due to less and cheaper parts.

In an aspect of the present invention an expression kit for extraction of breast milk from a female breast is presented, the expression kit comprising a funnel for receiving the breast therein, a housing, a container for receiving the breast milk, a connection port for connection to a vacuum source, and a membrane element arranged in the housing between the funnel and the container for sealing the funnel with respect to the connection port, the funnel with respect to the housing and the housing with respect to the container.

By way of the inventive layout of the expression kit, the handling becomes easy and straight forward for the user as well as easy to produce and assemble during production. The membrane element can be removed easily for cleaning by the user without complicated or expensive maintenance work. All parts of the expression kit are easily detachable and by way of the membrane element reliably sealable again. Due to the position of the membrane element there is no obstacle to view the position of the nipple in the funnel if the latter is transparent to allow better control.

The membrane further allows secure separation between the milk flow through the expression kit and the vacuum generated by the vacuum source, thus preventing breast milk to enter the vacuum system.

Preferred embodiments of the invention are defined in the dependent claims. It shall be understood that the claimed method has similar and/or identical preferred embodiments as the claimed device and as defined in the dependent claims.

Preferably, the membrane element comprises a body, sealing segments arranged on the body and a valve section. This allows all parts of the expression kit being sealed with respect to neighboring parts.

According to a preferred embodiment of the invention, the body, the sealing segments and the valve section are formed integrally, allowing easy production and assembly even for a non-specialist person.

Preferably, the body of the membrane element is substantially cylindrical with a longitudinal axis thereof being essentially parallel to a longitudinal axis of the housing. The shape of the membrane element allows easy assembly after cleaning since the orientation with respect to the housing is unambiguous.

The sealing segments are arranged on opposing ends of the body of the membrane element. Thus, a major part of the membrane element's body is available for transferring the vacuum to the breast.

According to a preferred embodiment, a first of the sealing segments is arranged between the funnel and/or the housing and the connection port, and wherein a second of the sealing segments is arranged between the housing and the container. By way of this, all parts of the expression kit are airtight sealable without complicated sealing elements which can be lost or damaged during cleaning or due to wrong placement during reassembly.

Advantageously, at least one of the sealing segments is collar-shaped for being clamped between the funnel and the housing and/or between the housing and the container. The collar-shape allows easy clamping between the adjacent parts of the expression kit.

Preferably, the valve section is arranged on the body of the membrane element with orientation towards the container. Thus, breast milk collected in the container can be prevented from flowing back towards the funnel and flooding the housing of the expression kit.

Preferably, the valve section comprises a one-way-valve, in particular a duckbill valve. Duckbill valves are easy valves without further components and thus easy to manufacture and to clean.

Advantageously, the membrane element comprises a vent for venting the container. Venting is important to allow the air contained in the container before expression starts to escape, because otherwise the air will counteract to the vacuum.

According to another embodiment of the invention, the membrane element comprises stiffening elements which extend substantially parallel to the body. By way of the stiffening elements the membrane element can be supported in its shape. This eases insertion into the housing and ensures the sealing functions of the membrane element.

Preferably, the stiffening elements are formed integrally with the body of the membrane element, thus making manufacturing and assembly easier, since only one part has to be inserted into the housing of the expression kit.

Alternatively, the stiffening elements are formed separately from the membrane element, preferably with a support structure, and are connected to the body and/or to the sealing segments of the membrane element. This embodiment is especially advantageous when the material of the membrane element is soft and rigid. The support structure helps to keep the membrane element's body in shape and ensures easy assembly. The support structure can comprise elements allowing connection to the sealing segements or directly to the body.

According to a preferred embodiment of the invention, the membrane element is formed of a resilient material, preferably from silicone. Silicone is well-established in the application to breast pumps and has proven to be the best choice for articles in the field of breast pumps.

BRIEF DESCRIPTION OF THE DRAWINGS

These and other aspects of the invention will be apparent from and elucidated with reference to the embodiment(s) described hereinafter. In the following drawings FIG. 2A shows a cross section of a second embodiment of an expression kit according to the invention, FIG. 2B shows a perspective exploded view of the expression kit of FIG. 2A.

DETAILED DESCRIPTION OF THE EMBODIMENTS

Figure 1A:
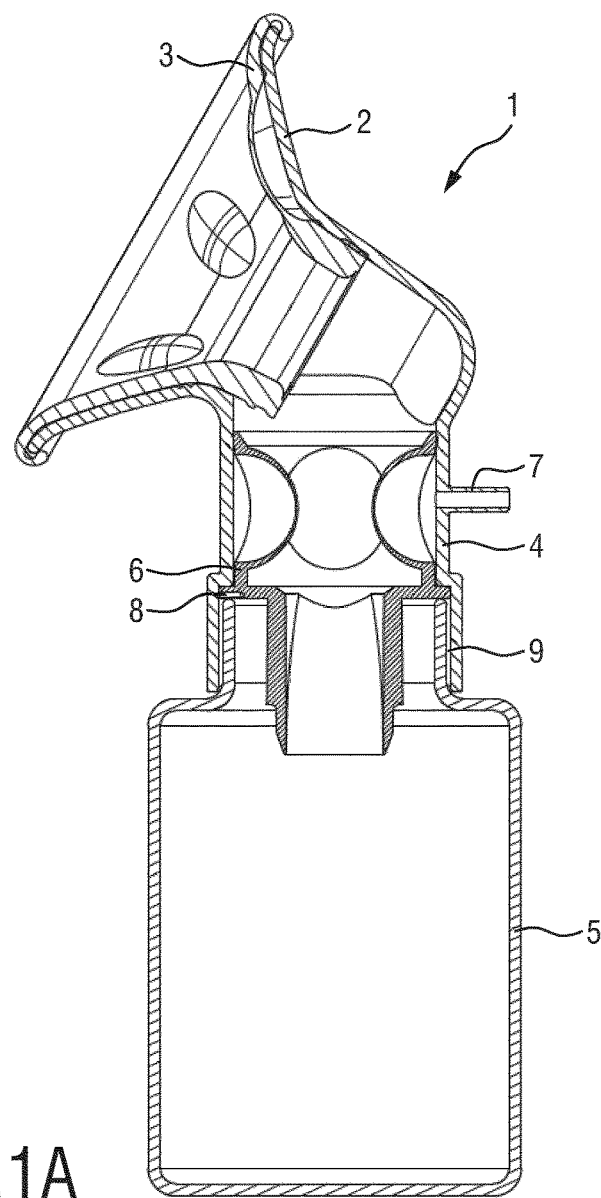
FIG. 1A shows a cross section of a first embodiment of an expression kit according to the invention.

FIG. 1A shows a first embodiment of an expression kit 1 according to the invention. The expression kit 1 comprises a funnel 2 which in the present embodiment is integrally formed with a housing 4 of the expression kit 1. A cushion 3 may be arranged in the funnel 2 to provide a comfortable feeling for the user. The funnel 2 and the cushion 3 are shaped to receive a user's breast therein.

The expression kit 1 further comprises a container 5 which might be connected to the housing 4 of the expression kit 1 by way of a connection 9 which might be a click or snap connection like a bayonet connection or by way of a screwing connection. A vent 8 is present between the housing 4 and the container to allow air to vent to the outside of the container 5.

The housing 4 of the expression kit 1 further comprises a connection port 7 to a vacuum source. The vacuum source may be any pumping device generally known in the arts, especially a mechanical or electrical pump or a manual pump.

According to the invention, the expression kit 1 is further equipped with a membrane element 6 which is arranged in the housing 4 of the expression kit 1. The inventive membrane element 6 fulfills different purposes. On the one hand, the membrane element 6 seals the fluid path of the expressed breast milk from the funnel 2 to the container 5 with regard to the vacuum source connected to the housing 4 of the expression kit 1. By way of this, it is prevented that breast milk enters the vacuum system with the consequence of possible failure of the pump and the necessity to clean the respective parts. On the other hand, the membrane element 6 is used as a sealing device between the housing 4 of the expression kit 1 and the container 5. Finally, the membrane element 6 features a valve function to prevent body milk being collected in the container 5 to backflow into the body part 4 of the expression kit or the funnel 2 with the risk of spilling.

In the following, the membrane element 6 is described in further detail with reference to FIG. 1B.

The membrane element 6 comprises a body portion 20. The body portion 20 is preferably shaped essentially cylindrical with a longitudinal axis being substantially parallel to a longitudinal axis of the housing 4 of the expression kit 1. The body portion 20 may comprise several dents 23 which support deformation of the body part 20 of the membrane element 6 when the vacuum source actuates the membrane element 6 via the connection port 7. The membrane element 6 by its deformation transfers the vacuum generated by the vacuum source to the breast in the funnel 2, thus extracting breast milk therefrom. In FIG. 1B, four dents 23 are provided, however, this is exemplary only and does not restrict the invention to this number. More or less dents 23 can be present if applicable.

Further, the membrane element 6 comprises two sealing segments 21 which are integrally formed with the body portion 20. The sealing segments 21 are configured to seal on the one hand the expression kit 1 with respect to the vacuum source and on the other hand the housing 4 of the expression kit 1 with respect to the container 5. As can be seen in FIG. 1B, a first or upper sealing segment 21a is formed like a circumferential ring on a first end of the body part 20 which is facing the funnel 2. The upper sealing segment 21a is in contact with the housing 4 of the expression kit 1. When a vacuum is supplied via the connection port 7, the membrane element 6 is deformed while the first sealing segment 21a is configured to stay in contact with the body part 4 by way of form fit. A second or lower sealing segment 21b is formed like a circumferential collar protruding from the body portion 20 of the membrane element 6. The collar is formed on a second end of the body portion 20 to be inserted and clamped between the housing 4 of the expression kit 1 and the container 5. In this position, the second sealing segment 21b provides a sealing function between the housing 4 and the container 5. The vent 8 mentioned with reference to FIG. 1A is shown in the perspective views in the middle and on the right of FIG. 1B. The vent 8 is provided in the collar of the second sealing segment 21b to allow venting of the container 5 to prevent the air in the container 5 to counteract to the vacuum.

The body portion 20 of the membrane element 6 further comprises a valve section 22 which is integrally formed with the body portion 20. The valve section 22 comprises a duckbill valve 24 as can be seen best in FIG. 1B on the right. The duckbill valve 24 is configured as a one way valve preventing breast milk collected in the container 5 to backflow towards the funnel 2. Thus, the expression kit 1 might be turned or shaken during expression without milk flowing unintentionally back towards the funnel 2. Without valve 24, the milk might be spilled and lost.

The membrane element 6 might be formed from any suitable resilient material like silicone which is easy to clean and cost effective in production. If the membrane element 6 fails, it can be easily replaced by the user of the expression kit 1 without costly maintenance work.

Turning now to FIGS. 2A and 2B, a second embodiment of the inventive expression kit 1 is described. For the sake of simplicity, same parts are referred to with same reference signs as in FIGS. 1A and 1B.

Figure 1B:
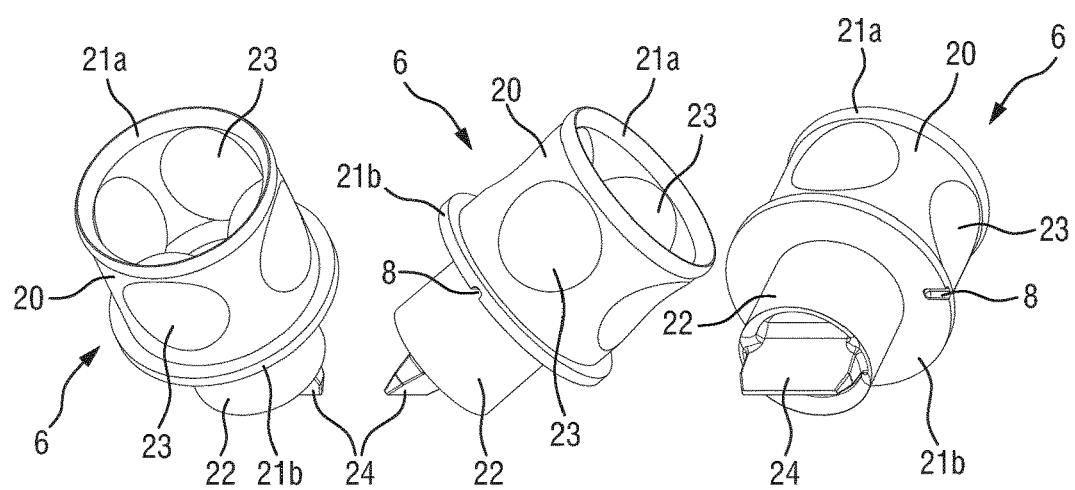
FIG. 1B shows three perspective views of a membrane element for the expression kit of FIG. 1A.

Similar to FIGS. 1A and 1B, the expression kit 1 comprises a funnel 2 shaped to receive a female breast therein. In contrast to FIG. 1A, the embodiment according to FIG. 2A comprises a funnel 2 which is detachable from the housing 4 of the expression kit 1. The funnel 2 can be connected to the housing 4 via a snap or click connection 9 or by screwing the funnel 2 on the housing 4. The expression kit 1 further comprises a container 5 and a connection port 7 for connection to a vacuum source. A cushion which is not shown in FIGS. 2A and 2B can be arranged in the funnel 2 for more comfort of the user.

Again, a membrane element 6 is present to fulfill the different functions of sealing and transferring the vacuum. In the embodiment according to FIG. 2A, the membrane element 6 is formed essentially cylindrical with a body portion 20, sealing segments 21, a valve section 22 and a duckbill valve 24. The body portion's 20 longitudinal axis is essentially parallel to a longitudinal axis of the housing 4. The respective parts of the membrane element 6 are best visible in the exploded view of FIG. 2B.

The sealing function of the membrane element 6 is fulfilled by two sealing segments 21a and 21b which are formed both collar-like comparable to the second sealing segment 21b of FIG. 1B. The first sealing segment 21a of FIG. 2B is used to seal the funnel 2 with respect to the housing 4 of the expression kit 1. This is visible in FIG. 2A adjacent to the connection 9 between funnel 2 and housing 4. The sealing is achieved by clamping the collar-like segment 21a between the funnel 2 and the housing 4. The second sealing segment 21b is used similarly to FIG. 1A to seal the housing 4 of the expression kit 1 with respect to the container 5, being clamped between the housing 4 and the container 5.

The transfer of the vacuum which is applied via the connection port 7 is again possible by deformation of the body portion 20 of the membrane element 6. In the embodiment according to FIGS. 2A and 2B, the body portion 20 of the membrane element 6 comprises two stiffening elements 25 which support the shape of the membrane element 6 and keep it in form for mounting in the housing 4. Again, the body portion 20, the sealing segments 21, the valve section 22 and the stiffening elements 25 are formed integrally from one suitable material like silicone. Alternatively, the stiffening elements 25 can be part of a separate component formed from another, preferably a stiffer material, thus supporting the rigid body 20 of the membrane element 6. The stiffening elements 25 can be formed with a support structure 26 which can be connected or fixed to the body 20 and/or the sealing segments 21.

Like in the embodiment according to FIGS. 1A and 1B, the membrane element 6 comprises a duckbill valve 24 to prevent breast milk collected in the container 5 from flowing backwards towards the funnel 2. The duckbill valve 24 is also integrally formed with the membrane element 6.

Figure 3A:
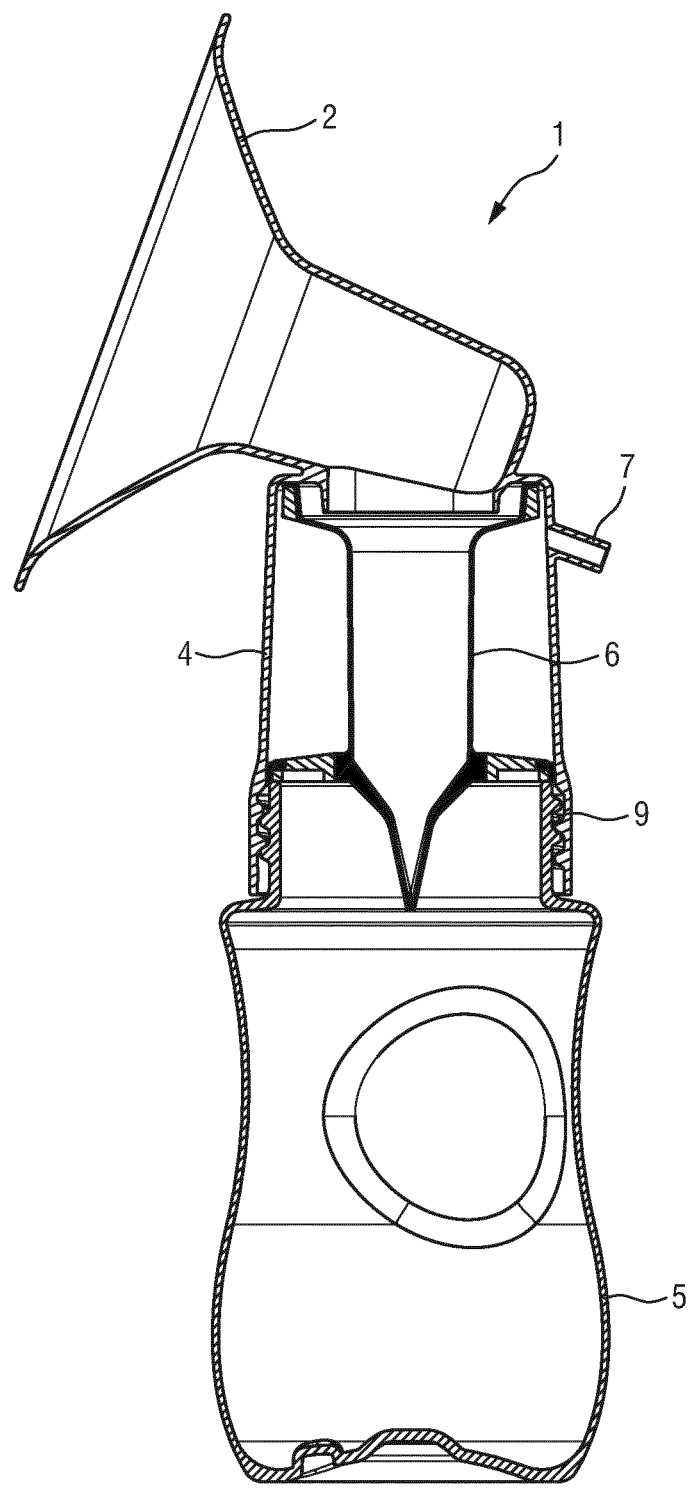
FIG. 3A shows a cross section of a third embodiment of an expression kit according to the invention.
Figure 3B:
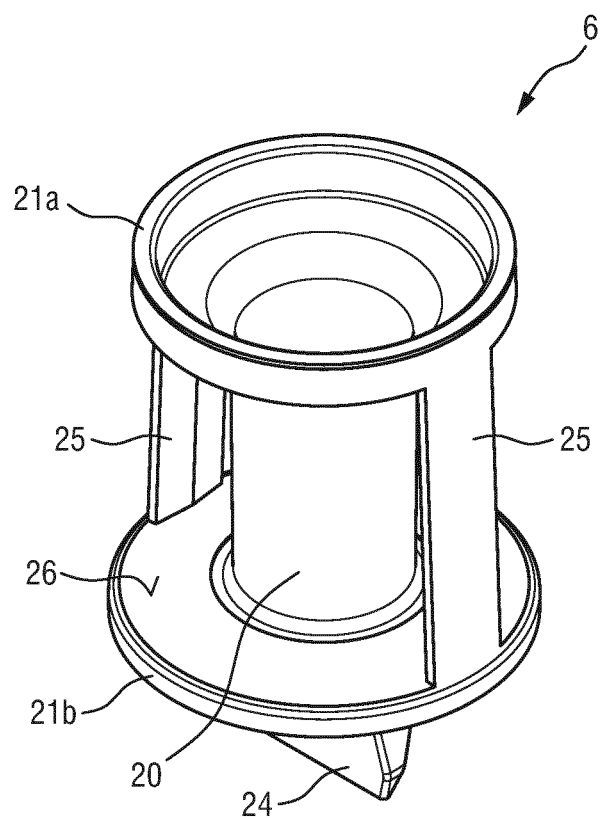
FIG. 3B shows a perspective view of a membrane element for the expression kit of FIG. 3A.

In FIGS. 3A and 3B yet another embodiment of the invention is shown. The third embodiment combines several features of the embodiments described with reference to FIGS. 1 and 2. Same parts are again referred to by same reference numbers. The function of the membrane element 6 of the third embodiment is the same as in the embodiments described before.

Like the embodiment according to FIG. 1A, the third embodiment shows a housing 4 with the funnel 2 attached to it. Accordingly, the upper sealing segment 21a of the membrane element 6 is formed in analogy to the upper sealing segment 21a of FIG. 1A. It is circular in shape and pressed against an inner wall of the housing 4.

The lower sealing segment 21b is again formed collar-like as e.g. in FIG. 2A, but with an angular portion extending from the collar in a direction substantially perpendicular to the collar or parallel to the body 20 of the membrane element 6. By way of this the sealing segment 21b can be clamped between the housing 4 and the container 5, but not in a horizontal direction as shown in FIG. 2A, but in a vertical direction. The sealing function is likewise fulfilled.

As already described with reference to FIG. 2B, the membrane element 6 may comprise stiffening elements 25. These can be formed integrally with the membrane element 6 if the material of the latter is stiff enough, otherwise, e.g. when silicone is used for the membrane element 6, the stiffening elements 26 may be formed from a different stiffer material to support the membrane element 6.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. Expression kit for extraction of breast milk from a female breast, comprising:
    a funnel for receiving the breast therein,
    a housing,
    a connection port for connection to a vacuum source, and
    a membrane element arranged in the housing between the funnel and a container for sealing the funnel with respect to the connection port, the funnel with respect to the housing and the housing with respect to the container, whereby the container is intended to receive the breast milk,
    wherein the membrane element comprises a body, sealing segments arranged on the body, and a valve section configured for the flow of the breast milk from the housing to the container through the valve section,
    wherein the body, the sealing segments and the valve section are formed integrally,
    wherein the body of the membrane element is substantially cylindrical with a longitudinal axis thereof being essentially parallel to both a longitudinal axis of the housing and a longitudinal axis of the container.

2. Expression kit according to claim 1, wherein the sealing segments are arranged on opposing ends of the body of the membrane element.

3. Expression kit according to claim 1, wherein a first of the sealing segments is arranged between the funnel and/or the housing and the connection port, and wherein a second of the sealing segments is arranged between the housing and the container.

4. Expression kit according to claim 1, wherein at least one of the sealing segments is collar-shaped for being clamped between the funnel and the housing and/or between the housing and the container.

5. Expression kit according to claim 1, wherein the valve section is arranged on the body of the membrane element with orientation towards the container.

6. Expression kit according to claim 5, wherein the valve section comprises a one-way-valve, optionally a duckbill valve.

7. Expression kit according to claim 1, wherein the membrane element comprises a vent for venting the container.

8. Expression kit according to claim 1, wherein the membrane element comprises stiffening elements which extend substantially parallel to the body.

9. Expression kit according to claim 8, wherein the stiffening elements are formed integrally with the body of the membrane element.

10. Expression kit according to claim 8, wherein the stiffening elements are formed separately from the membrane element, optionally with a support structure, and are connected to the body and/or to the sealing segments of the membrane element.

11. Expression kit according to claim 1, wherein the membrane element is formed of a resilient material, optionally from silicone.

12. Expression kit according to claim 1, wherein the body of the membrane element is deformable when the membrane element is actuated by vacuum generated by the vacuum source via the connection port.

13. Expression kit according to claim 12, wherein the body of the membrane element comprises dents that support deformation of the body of the membrane element.

14. Expression kit according to claim 12, wherein at least one of the sealing segments is in contact with the housing prior to and during deformation of the body of the membrane element.

15. A breast pump comprising an expression kit as claimed in claim 1, and a pumping device in communication with the expression kit.

16. Expression kit for extraction of breast milk from a female breast, comprising:
    a funnel for receiving the breast therein,
    a housing,
    a connection port for connection to a vacuum source, and
    a membrane element arranged in the housing between the funnel and a container for sealing the funnel with respect to the connection port, the funnel with respect to the housing and the housing with respect to the container, whereby the container is intended to receive the breast milk,
wherein
    the membrane element comprises a body, sealing segments arranged on the body, and a valve section configured for the flow of the breast milk from the housing to the container through the valve section,
    the body, the sealing segments and the valve section are formed integrally,
    the body of the membrane element is substantially cylindrical with a longitudinal axis thereof being essentially parallel to a longitudinal axis of the housing,
    a longitudinal axis of the funnel is angled towards the longitudinal axis of the body of the membrane element.

17. Expression kit for extraction of breast milk from a female breast, comprising:
    a funnel for receiving the breast therein,
    a housing,
    a connection port for connection to a vacuum source, and
    a membrane element arranged in the housing between the funnel and a container for sealing the funnel with respect to the connection port, the funnel with respect to the housing and the housing with respect to the container, whereby the container is intended to receive the breast milk,
    wherein the membrane element comprises a body, sealing segments arranged on the body, and a valve section configured for the flow of the breast milk from the housing to the container through the valve section, the valve section comprising a one-way valve,
    wherein the body, the sealing segments and the valve section are formed integrally,
    wherein the housing has an open end or an aperture within or through which the valve section is arranged,
    wherein the body of the membrane element is substantially cylindrical with a longitudinal axis thereof being essentially parallel to a longitudinal axis of the container.

18. Expression kit according to claim 17, wherein a longitudinal axis of the funnel is angled towards the longitudinal axis of the body of the membrane element.

19. Expression kit according to claim 17, wherein the membrane element comprises stiffening elements which extend substantially parallel to the body.

* * * * *